(12) United States Patent
Breitenstein et al.

(10) Patent No.: US 9,375,140 B2
(45) Date of Patent: Jun. 28, 2016

(54) TOPOGRAPH

(71) Applicant: HAAG-STREIT AG, Koeniz (CH)

(72) Inventors: Joerg Breitenstein, Zollikofen (CH); Jonas Haehnle, Bern (CH); Christian Zoss, Belp (CH); Peter Stalder, Brittnau (CH); Kaspar Baltzer, Bern (CH); Ernst Rindlisbacher, Boll (CH); André Meznaric, Bern (CH); Christian Schlaeppi, Bern (CH); Lucio Robledo, Bern (CH)

(73) Assignee: HAAG-STREIT AG, Koeniz (CH)

( * ) Notice: Subject to any disclaimer, the term of this patent is extended or adjusted under 35 U.S.C. 154(b) by 176 days.

(21) Appl. No.: 14/164,020

(22) Filed: Jan. 24, 2014

(65) Prior Publication Data
US 2014/0204339 A1    Jul. 24, 2014

(30) Foreign Application Priority Data

Jan. 24, 2013 (EP) .................................... 13405008

(51) Int. Cl.
A61B 3/10 (2006.01)
A61B 3/107 (2006.01)
A61B 3/14 (2006.01)

(52) U.S. Cl.
CPC ............... *A61B 3/1005* (2013.01); *A61B 3/107* (2013.01); *A61B 3/14* (2013.01)

(58) Field of Classification Search
CPC .......... A61B 3/102; A61B 3/103; A61B 3/14; A61B 3/107; A61B 3/13
USPC .................. 351/212, 211, 205, 246, 208, 210
See application file for complete search history.

(56) References Cited

U.S. PATENT DOCUMENTS

| | | | |
|---|---|---|---|
| 5,526,073 A * | 6/1996 | Mattioli | A61B 3/107 351/205 |
| 7,246,905 B2 * | 7/2007 | Benedikt | A61B 3/107 351/210 |
| 2006/0147189 A1 | 7/2006 | Yogesan et al. | |
| 2009/0268209 A1 | 10/2009 | Waelti et al. | |
| 2010/0118270 A1 | 5/2010 | Shea et al. | |

FOREIGN PATENT DOCUMENTS

| | | |
|---|---|---|
| DE | 19852331 A1 | 5/2000 |
| EP | 1946039 B1 | 4/2009 |

* cited by examiner

*Primary Examiner* — Hung Dang
(74) *Attorney, Agent, or Firm* — Birch, Stewart, Kolasch & Birch, LLP

(57) ABSTRACT

An adapter (60) for an apparatus (50) for measuring a first property of an eye is attachable to the apparatus (50), wherein, when the adapter (60) is attached to the apparatus (50), a second additional property of the eye is measurable.

23 Claims, 3 Drawing Sheets

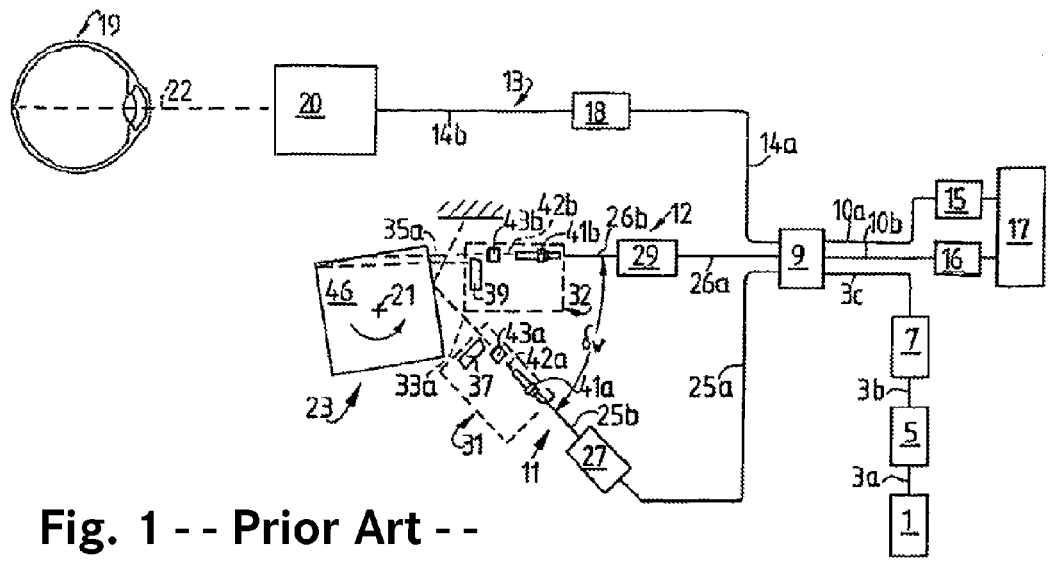
Fig. 1 -- Prior Art --
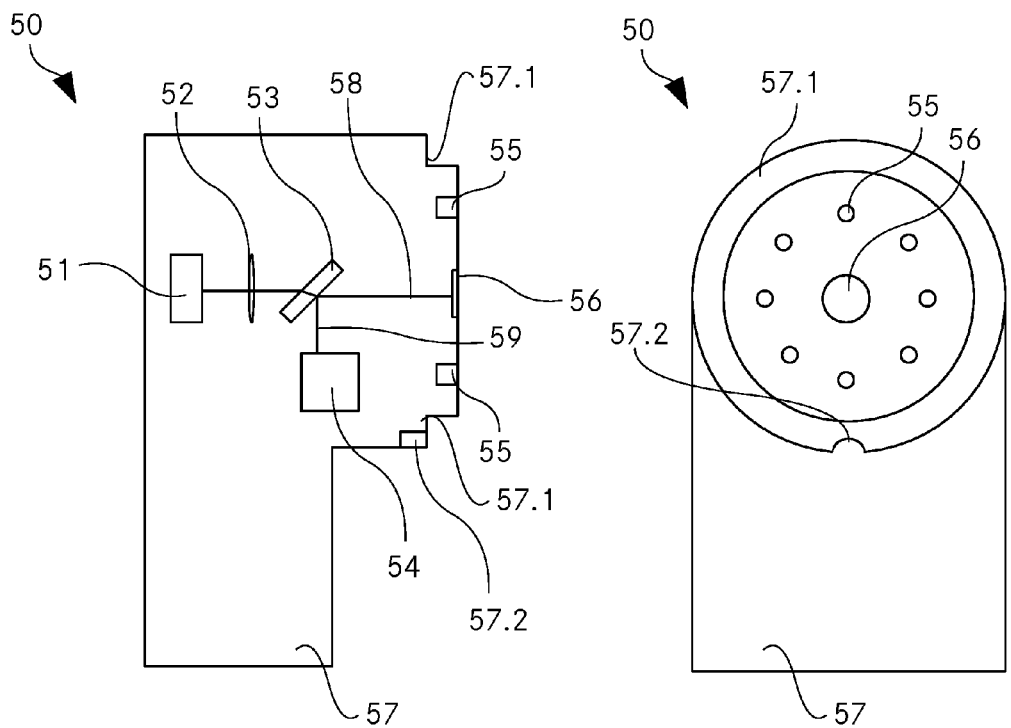
Fig. 2  Fig. 3

TOPOGRAPH

TECHNICAL FIELD

The invention relates to an adapter for an apparatus for measuring a first property of an eye. The invention furthermore relates to an arrangement for measuring properties of the eye, comprising an adapter and apparatus for measuring a first property of the eye. Finally, the invention relates to a method for operating the arrangement.

PRIOR ART

For optimally fitting intraocular lenses (IOLs) it is necessary to determine the geometric properties of the eye on which the operation is to be carried out with a high degree of accuracy before the operation takes place. Usual formulae for fitting IOLs are based for one on axial distances of the eye, such as for example eye length and anterior chamber depth, and also on the radii of curvature of the boundary surfaces, in particular radius of curvature arid axis of the flattest and the steepest meridian of the cornea front face.

For the purposes of distance measurements, nowadays interferometric or cross-section-generating methods are used for example in the front eye section, in particular a slit-like illumination of the cornea in connection with the imaging of a cross-section onto a camera whose sensor and lens are arranged in Scheimpflug geometry.

In order to determine the radii of curvature of the eye, reflectometry methods are usually used, which are based on the imaging of the specular reflections of the known light pattern onto a digital camera sensor, which are caused by the cornea front face (or by other structures of the eye).

In a further method, a slit-like illumination is guided laterally over the eye; the topography of the illuminated by structures can in turn be determined by analyzing the reflection images.

It is possible in principle to combine measurements of these complementary, data (axial distances and curvatures) within the same device. For example, devices such as the Lenstar LS900 (Haag-Streit) or IOL Master (Zeiss) are capable of carrying out axial length measurements in the eye as well as keratometry measurements (curvature and axis of the steep and flat meridian). Patent specification DE19852331 (A1) furthermore discloses the combination of Placido ring topography measurement and time domain optical coherence tomography.

However, said devices have the disadvantage that they are restricted to one specific implementation of the individual types of device.

Such a device for exactly determining eye lengths and topographies additionally requires either a significantly shorter working distance (which makes measurement more difficult for restless patients and increases the risk of collision of the measurement device with the eye) or a significantly greater device diameter, which makes it difficult to keep visual contact between the operator and the patient and results in increased collision risk between measurement device and forehead or nose region of the patient.

In order to determine the parameters required for IOL fitting, such as axial eye length and cornea curvatures, the prior art thus requires at least two specialized measurement devices, inflexible combination devices or expensive and complicated 3D tomographs. Said solutions are not satisfactory, either under ergonomic or economic aspects. It is furthermore not possible according to the prior art to flexibly adapt the measurement method to the patient and to find an individual compromise for working distance, minimum glare for the patient, information content and accuracy of the measurement.

REPRESENTATION OF THE INVENTION

It is the object of the invention to provide an arrangement for measuring properties of an eye that is part of the technical field stated in the introduction, which arrangement has a particularly simple construction, can be used variably and is cost-effective.

The object is achieved by the features of claim 1. According to the invention, the adapter is attachable, preferably releasably, to the apparatus, and wherein, when the adapter is attached to the apparatus, the second property of the eye is measurable.

The term adapter will be understood below to mean a device, an add-on module or the like, with which, in relation to the apparatus, a property can be measured that cannot be measured with the apparatus alone, that is to say cannot be measured without the adapter or not with the same quality. The properties which can be measured by the apparatus preferably differ from those properties that can be measured with the apparatus using the adapter.

The adapter is preferably configured such that it can use resources of the apparatus. As a result, specific components, which are necessary for measuring the first and the second properties, can be used for both measurements such that the device can be manufactured particularly cost-effectively.

The possibility of using said apparatus optionally with the adapter for different measurement methods also reduces the risk of systematic measurement errors. Also made possible thereby is the referencing of the measurements on the basis of (virtually) simultaneously detected common data and an improvement of the comparability of the data. Specifically, this results in the possibility of analyzing the ascertained data of the first and second properties combined and thus of being in a position to efficiently make more detailed statements relating to the measurement object. Furthermore, the overall duration of the measurements will thus be reduced to a minimum to the advantage of patients and medical personnel.

Moreover, the arrangement requires no additional placement area but merely a storage space for the adapter. The clinical workspace can therefore be optimally utilized. Furthermore, visual contact to the patient is not necessarily restricted by the adapter during the measurement of the first property.

The adapter can be provided as an additional device for existing apparatuses for measuring the first property of an eye. Furthermore it is possible for a plurality of different adapters to be provided for the apparatus, which make possible measurements of different properties of an eye. On account of the modular construction, a customer purchasing the apparatus will furthermore have the option of deciding to purchase the adapter for the measurement of the second property of the eye at a later date.

The arrangement, comprising the apparatus and the adapter, is furthermore advantageous if different working distances are necessary for the measurement of the two properties. For example, the adapter and the apparatus can be configured such that a shorter distance from the measurement object is necessary for the second property, wherein the shorter distance can be achieved by positioning the adapter.

The statement that the second property of the eye is measurable with the adapter attached to the apparatus should not necessarily be interpreted to mean that the first property is measurable only if the adapter is not attached to the apparatus.

It is conceivable that the adapter attached to the apparatus is switchable between an active state and the passive state. However, in one preferred embodiment, the adapter is configured as a removable add-on element for the apparatus. In one preferred embodiment, with the adapter attached, the first and the second property can be measured in particular simultaneously, or, respectively, at the same time. Typically, the adapter for the measurement is attached between a patient and the apparatus to the apparatus.

A person skilled in the art will know that, rather than the eye, it is also possible using the apparatus and the adapter to examine a model of an eye, for example a glass eye, a lens system or generally a body which is light transmissive at least partially, at least at one wavelength, in respect of the two properties.

The property is preferably a measurable optical property, wherein optical does not exclusively mean the visual part of the optical spectrum. The optical property may also comprise a spectrum in the infrared or ultraviolet spectral range. However, in variants, other properties, which are measurable for example by acoustic measurement methods such as ultrasound, can be measured. The optical properties are preferably lengths, curvatures, topographies etc.

The term measurement is understood to mean the determination of a parameter, which is understood to mean in particular a quantitative, substantially continuous measurement or a discrete measurement, but also a binary measurement such as satisfied/not satisfied etc.

The first and/or the second property is preferably a geometric property of the eye. Various measurements can thus be carried out with an apparatus using the adapter, where the measurement data can be used for example to characterize an eye. A geometric model of an eye, for example, can be established therewith.

In variants, the first and/or the second property can also comprise for example a refractive index, a colour spectrum, a location-dependent refractive index, scatter, reflection or absorption coefficients, a colour spectrum, also in each case as a function of the polarization and the like.

The first property preferably comprises a distance within an eye and the second property comprises at least a topography or a curvature of the eye. A three-dimensional model of the measured eye can be established therewith. The model can, for example, be used for the fitting of intraocular lenses or for supporting operations on the eye. Furthermore, such models can also be used to simulate beam paths through the eye. In principle, further properties can also be captured using the apparatus or the adapter, a person skilled in the art will be aware in particular that derived variables can also be ascertained from these data, such as for example a volume and the like.

In variants, the first property can also comprise a topography, and the second property a distance within the eye.

The adapter can be configured for example as a reflectometry module, which comprises a structure that forms a light pattern for drawing conclusions as to its geometric properties on the basis of the reflection of said pattern through the eye. The reflectometry module is in this case realized as a preferably removable adapter for use on an apparatus, or respectively a device for axial distance measurement in the eye, wherein the reflectometry module need not necessarily comprise all necessary components to enable autonomous operation.

The first property preferably comprises at least one of the following lengths: cornea thickness, anterior chamber depth, lens thickness, eye length. The first property can of course also comprise a further data, in particular lengths, such as for example the depth of the posterior eye chamber etc. A person skilled in the art will know that in a measurement of various lengths, further ones can also be derived directly, with the result that they can also be determined indirectly. It is likewise possible using known data, for example empirically ascertained length ratios, to deduce further lengths, In variants, the first property can also comprise other properties instead of the lengths, such as for example topography data.

The adapter preferably comprises coupling means with which the adapter is attachable to the apparatus, wherein the coupling means preferably comprise a magnet. The coupling means preferably make possible simple mounting and removal of the adapter to and from the apparatus. As a result, it is possible to switch efficiently between the two measurement modi, specifically between the measurement of the first property, or further properties that can be captured by the apparatus, and the second property. It is thus possible, for example, to carry out a keratometric measurement while the adapter is removed and a topography measurement while the adapter is attached, whereas it is possible to measure lengths in both cases (while the adapter is attached and also while it is removed).

Particularly preferably, the coupling means additionally comprise a magnet with which attachment and removal of the adapter can take place particularly efficiently. To this end, the apparatus preferably comprises a magnet. The adapter can additionally be held in place on the apparatus via a form fit. The form fit is preferably configured such that the adapter can be attached in exactly one orientation on the apparatus in a functional manner. This can be achieved in various ways, for example the adapter can have two pins of different diameters, and the apparatus can have corresponding holes for receiving the pins. The form fit can also be configured as a tongue-and-groove connection. The tongue-and-groove connection can also be configured in the shape of an arc. Owing to the use of the magnets, the form fit may be configured as a positioning aid and only partially as a connecting apparatus. It is furthermore expedient to dimension the mechanical holding forces such that the adapter is coupled to the apparatus only when it is completely in the completely placed-on state, for example by suitably choosing the composition, size and the position of the permanent magnets used for the coupling.

However, a person skilled in the art will know that the adapter can also be attached to the apparatus via a clip closure, bayonet closure and other reversible connecting methods known to the person skilled in the art, wherein it is also in particular possible to omit the magnet.

Attachment of the adapter must not necessarily be carried out in an efficient manner, but can under certain circumstances certainly also be less complicated. In this case, a device may be provided with which the adapter can be positioned between a measurement position and a passive position, in which the first property can be measured (see further below in this respect).

In variants, it is also possible for only the apparatus to comprise coupling means for attachment of the adapter. Furthermore, it is also possible for the adapter or for the adapter and the apparatus to be provided with a magnet—however, in this case the permanent magnet of the adapter may prove disruptive during handling, since it would attract magnetic materials.

The adapter preferably comprises a first optical waveguide for the structured illumination of the eye. On the basis of the reflections attained by the structured illumination, it is possible to draw conclusions regarding the two properties of the eye. In particular, geometric properties, such as for example a topography of the eye, in particular the cornea, can be achieved. To this end, the adapter can project a plurality of regularly or irregularly arranged points onto the eye via the optical waveguide. Instead of the points, it is also possible to project rings, or Placido rings. The topography of the cornea can be determined on the basis of the patterns reflected by the cornea. A person skilled in the art will know further patterns with which the same purpose, that is to say measurement of the cornea topography, can be achieved. This measurement principle is often referred to as reflectometry measurement—this term also includes videokeratometry, which uses point projection, and the Placido ring topography, which projects concentric rings.

The advantage of the surface-type illumination with the Placido ring method resides in the high sampling density and in the ability to capture complete topographyies. Furthermore, the Placido ring topography provides a highly detailed model of the cornea surface. It also makes possible local evaluation of the radii of curvature at each point (with the exception of the central region), such that the cornea front face can be largely reconstructed. On the basis of the measured data, for example, the diagnosis of further pathologies such as irregular astigmatism is made possible.

With point-type illumination, it is easier to detect the reflections of eye structures located more deeply (Purkinje reflections) and thus to also determine radii of curvature for example of the cornea rear face and the eye lens front and back faces. Compared to the lateral positioning errors, keratometry measurements with point-type illumination provide a very robust result with excellent repeatability of the measurement results, they provide an easily quantifiable and thus comparable result, and have therefore evolved into a standard method in the preparation for cataract operations.

Depending on application, preference is therefore given to the Placido ring method or the point method.

It is alternatively possible to obtain radii of curvature also through methods for coherence reflectometry if the light beam used for measurement is deflected laterally in a controlled manner and the obtained data are joined to form volume images. However, devices according to this method are very complex and expensive. Finally, the radii of curvature of the eye can also be determined on the basis of cross-section images. In a further method, slit-type illumination is guided laterally over the eye; the topography of the illuminated eye structures can in turn be determined through analysis of the reflection images.

The adapter preferably comprises a second optical waveguide for diffuse or indirect illumination of the eye. The illumination direction is to this end preferably chosen such that a radial distance from the measurement axis is chosen to have a sufficient size such that the direct reflection through the cornea does not influence the measurement of the properties of the eye, but the eye is still optimally illuminated. The light source does not necessarily have to be comprised by the adapter, it is also possible to use a light source of the apparatus using the second optical waveguide.

The adapter can also comprise further optical waveguides with which the eye can be illuminated simultaneously diffusely or indirectly for example from a plurality of sides.

The adapter preferably comprises a second optical waveguide with which the light from a light source of the apparatus or of the adapter is guidable onto the eye for diffuse and/or indirect illumination.

In variants, an illumination device for diffuse or indirect illumination can also be comprised by the adapter. In this case, it is also possible to dispense with the second optical waveguide.

Preferably, only the apparatus comprises a light source in the form of one or more LEDs, since they are cheap and compact and are available for practically any desired spectra. In variants, it is also possible to use laser diodes which emit light in the visible or infrared spectral range. A person skilled in the art will also know further suitable light sources.

The apparatus preferably comprises a light source, and the adapter comprises a first optical waveguide, such that in the case of an adapter that is attached to the apparatus, light from the light source is guidable to the eye via the first optical waveguide. The light source of the apparatus can thus be used both for the measurement of the first and of the second property of the eye, or can assist therein. Here, the LEDs can be used for example as positioning aids, for documentation and/or for the keratometry/topography measurement. It is thus possible to save further resources, as a result of which a simple and cost-effective construction of the adapter can be achieved.

In variants, the light source can also be comprised by the adapter. In this case, the first optical waveguide can, under certain circumstances, be dispensed with.

The apparatus preferably comprises a detector, preferably an image-recording unit, with which a second property of the eye is measurable with an adapter that is attached to the apparatus. As a result, a single detector of the apparatus can be used for data acquisition. The adapter, or the arrangement, thus becomes cheap in terms of construction, since the same detector can be used for the measurement both of the first and the second property. The image-recording unit is preferably a digital camera system.

In variants, rather than the apparatus, it is also possible for the adapter to comprise a detector. The shared components can also, for example, be represented only by the used processor for data processing or a data output unit, such as a printer, a screen or the like.

The apparatus preferably comprises a sensor for detecting the adapter. The sensor can be configured for example as a signal transmitter, which transmits a signal to a data processing device as soon as the adapter is identified as being "attached" to the apparatus and/or when the already attached adapter is moved into an operating position in which the second property of the eye can be measured. The sensor can preferably likewise be used to detect if the adapter is no longer attached to the apparatus, or is no longer in the operating position for measurement of the second property of the eye, whereupon a signal is likewise output. It is thus possible for example to switch an operating mode of the arrangement between measurement of the first property and measurement of the second property.

The apparatus preferably comprises a control unit with which, in dependence on a measurement value of the sensor, a measurement mode for the first property of the eye or a measurement mode for the second property of the eye is switchable. It is thus possible to automatically swap between the two measurement modi. In this case, the sensor can monitor the presence of the adapter, or check if the adapter is mounted. In addition, it is also possible to check merely if the adapter attached to the apparatus is in a position in which the second property can be measured. The sensor can be configured as a mechanical, inductive, electrical contact sensor and the like.

It is alternatively possible to dispense with automatic switching of the measurement mode, for example if both the first and the second property of the eye can be measured, or possibly both can be measured simultaneously, with the adapter being in the same position in the arrangement.

The apparatus preferably comprises an interferometer, preferably a Michelson interferometer. Use of an interferometer makes it possible in a simple manner to carry out length measurements in the eye. The optical interferometry for the axial distance measurement in the eye also has the advantage that it has a high measurement accuracy.

In addition, the measurement principle is contactless and thus particularly easy to operate. In particular, the contactless measurement is also not unpleasant for the patient.

For the measurement with an apparatus based on a Michelson interferometer, the eye of the patient is moved into its first beam path (sample arm). The length of the second beam path (reference arm) serves as a reference for the interference measurement. Analogously, the radiation can also first run through a Michelson interferometer with variable path length difference and subsequently be brought onto the patients eye.

In variants, instead of the above-described interferometers, it is also possible to use a tomography or a sonograph or the like. A person skilled in the art will know that other interferometer types can be used instead of the Michelson interferometer - for example a Mach Zehnder interferometer or the like.

For the interferometry length measurements, basically the following two options exist:
- time domain (TD) coherence reflectometry uses a reference arm with variable length and a light source with a short coherence length. For distance measurement, the reference arm length is continuously varied; as soon as the optical path length in the reference arm within one coherence length corresponds to an optical path length in the sample arm, interference can be observed.
- in Fourier domain (FD) coherence reflectometry, on the other hand, with a constant reference arm length, the interference signal is detected as spectrally resolved; spectral resolution can in this case be achieved by utilizing a spectrally broadband light source and decomposing the interference signal for example using a spectrometer into its spectral components (spectral domain (SD) coherence reflectometry), or by utilizing a narrow band light source which can be tuned over a frequency interval and detects the interference signal as a function of the source frequency. The structure of the analysed sample then results from the Fourier transform of the spectrally resolved interference signal.

The interferometer is preferably configured as a Fourier domain interferometer, since Fourier domain interferometers have a higher sensitivity with respect to time domain interferometry.

Alternatively, the interferometer can also be configured as a time domain interferometer.

The interferometer or at least the beam path of the sample arm is preferably pivotable and/or movable laterally with respect to the eye. A plurality of laterally offset and/or tilted distance measurements can thus be combined to form a volume image. This can be achieved for example by inserting a pair of galvanically operated scanning mirrors into the beam path. A person skilled in the art will therefore clearly know that such a movement of the measurement axis can also be achieved for example by moving the fixing aid for the eye or mechanically moving the entire arrangement.

In variants, lateral displaceability or pivotability can also be dispensed with.

The arrangement preferably comprises a pivot pin, with which the adapter is pivotably connectable to the apparatus. On account of this, the adapter can, if required, be moved into the beam path of the apparatus and measurements of the second property of the eye can be carried out. What is advantageous here is that the adapter is always ready. The pivot pin can comprise pivot positions that are defined for the measurement of the second property and for the measurement of the first property. Said pivot positions can be pre-defined, for example, by latching portions, with which the operation of the arrangement can be simplified. The axis position can be fixed for example by a permanent magnet. The pivot pin can in principle have any desired orientation, although it is preferably vertically arranged, since gravitational influences can thus be avoided.

In variants, the pivot pin may also be dispensed with.

In a method for measuring properties of an eye using an arrangement comprising an adapter and an arrangement for measuring a first property of the eye, wherein the adapter is attachable, preferably releasably, to the apparatus, the adapter is positioned in a beam path of the apparatus for measurement of the second property of the eye.

The method can furthermore comprise the following steps:
- measurement of a first property of the eye for obtaining first measurement values;
- controlling, in particular positioning, the adapter in dependence on the first measurement values.

Is thus possible to achieve synergies between the apparatus and the adapter. In a method for ascertaining the topography of the eye (curvatures etc) on the basis of the reflection image of structured illumination, knowledge relating to the distance of the structured light source (adapter) from the reflecting structure, that is to say the eye, is required. Interferometric distance measurement of the apparatus is now preferably used for this purpose, in particular since interferometric distance measurement is particularly precise.

This distance can alternatively also be ascertained by way of triangulation or cross-section recordings etc.

The apparatus is preferably used to determine a length of the eye and to set and/or monitor the position of the adapter on the basis of the length of the eye.

Owing to the attachment of the adapter, for example of the reflectometry module, the distance between the arrangement (apparatus and adapter) and the eye of the patient is reduced. In order to minimize the risk of collision between the eye of the patient and the adapter, it is possible to configure a control and analysis unit such that the distance measurement of the apparatus is continuously active and, if the distance from the eye (taking into account the dimensions of the adapter) falls below a critical distance, an acoustic, optical or mechanical alert is output.

The position can alternatively also be monitored and adjusted manually.

The arrangement preferably comprises a positioning apparatus for positioning, preferably automatically, the apparatus and/or the adapter in relation to the eye.

The apparatus preferably comprises a motorized XYZ adjustment stage. Said adjustment stage can be used to position the measurement head or the entire apparatus. With knowledge of the dimensions of the adapter and the apparatus, it is possible in this case to use the control unit to bring the measurement head of the apparatus with the adapter into an optimum measurement position, while avoiding collisions with the patient, on the basis of the distance information of the apparatus and/or of the information obtained from the image recording unit.

If the apparatus has a positioning apparatus, the control unit can also be used to balance out, using the positioning apparatus, any deviations of the measurement position occurring between sequential measurements on the basis of the distance information of the apparatus and/or of the information obtained from the image recording unit and thus to maintain a selected measurement position.

In summary it should be noted that the arrangement according to the invention consists of two mechanically separable apparatuses.

In one embodiment of the invention, the apparatus serves for measuring axial distances within the eye and furthermore contains an imaging optical unit, an image recording unit and a control and analysis unit. The apparatus preferably comprises an interface, for example a USB interface or a wireless connection or the like, to a PC (personal computer). Control of the measurement and evaluation of the data can thus be carried out using the PC. However, the apparatus likewise preferably comprises an electronic system, which contains fast closed-loop control circuits and data acquisition. In variants, all functionalities can also be implemented in an all-in-one device, wherein the apparatus carries out the control and the evaluation of the data. In this case, a connection of the apparatus to a separate PC may be dispensed with.

The adapter comprises at least one unit for structured illumination of the eye, which can be attached between the apparatus and the eye. The at least one light source, which serves the at least one unit for structured illumination of the eye, can be located in the apparatus and/or in the adapter.

Further advantageous embodiments and feature combinations of the invention result from the following detailed description and the entirety of the patent claims.

BRIEF DESCRIPTION OF THE DRAWINGS

The drawings used to explain the exemplary embodiment illustrate:

FIG. 1 a schematic illustration of an apparatus for interferometric measurement of lengths in eyes, according to the prior art;

FIG. 2 a schematic illustration of a cross section of an apparatus for interferometric measurement of lengths, along an optical axis;

FIG. 3 a schematic front view of an apparatus according to FIG. 2 in the direction of the optical axis;

In principle, identical parts are provided with the same reference signs throughout the figures.

WAYS OF CARRYING OUT THE INVENTION

Figure 4:
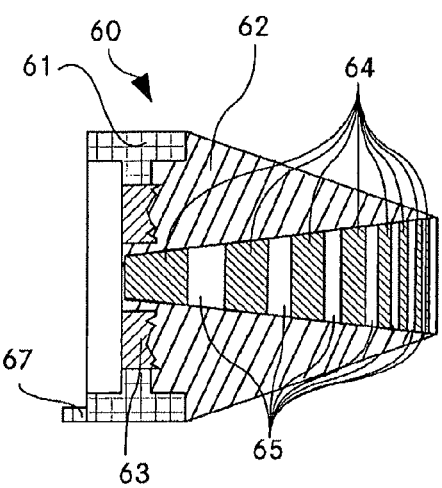
FIG. 4 a schematic illustration of a cross section of an adapter for Placido ring projection, along the optical axis.

The apparatus for measuring axial distances within the eye can be based for example on the time domain coherence reflectometry method, as is also implemented in Biometer Lenstar LS 900 from Haag-Streit AG and described in detail in EP 194 6039 B1.

FIG. 1 schematically illustrates a possible construction of said apparatus. However, the invention is not at all restricted to this method, but may just as well be implemented, for example, using spectral domain or swept source coherence reflectometry. The apparatus can also have a plurality of measurement regions and/or a plurality of interferometers.

FIG. 1 illustrates an exemplary embodiment of the apparatus according to the invention having an optical arrangement in the manner of a "Michelson interferometer". In this arrangement, the apparatus has a radiation source 1, the radiation of which has a short coherence length. The coherence length is significantly shorter than the thicknesses and path lengths to be measured, and ranges from 2 µm to 100 µm. Typically, operation takes place in a range of 10 µm to 20 µm. The shorter the coherence length, the more accurate the measurement, For this reason, a radiation source 1 having as broadband an output radiation as possible will likely be selected. Possible radiation sources 1 to be used are superluminescence diodes (SLD), light-emitting diodes (LEDs), white light sources or light sources having amplified spontaneous emission ((ASE), for example the radiation of a diode-pumped solid state body). This radiation is coupled into a monomode fibre 3a.

The monomode fibre 3a is guided to a radiation attenuator 5. The radiation attenuator 5 can be for example a loss splice between two monomode fibres, which are not illustrated. The radiation attenuator 5 can be used to attenuate the radiation that is reflected back in the direction to the radiation source 1 from the reference arms described below and from the measurement arm, Radiation reflected back into the radiation source 1 could for example negatively influence the emission behaviour in an SLD, an ASE or in a diode-pumped solid state body. The radiation attenuator 5 thus serves to minimize said negative influence. The radiation from the radiation source 1, which may now be attenuated, is guided from the radiation attenuator 5 into a monomode fibre 3b to a polarization controller 7. The polarization controller 7 is used to set the polarization state of the radiation running through the controller. The radiation attenuator 5 and the polarization controller 7 are optional and not absolutely necessary for the apparatus according to the invention.

The radiation from the radiation source 1 is guided further using a monomode fibre 3c onto a 3×3 monomode fibre coupler 9. The monomode fibre coupler 9 is used to split the radiation from the radiation source 1 into two reference arms 11 and 12 and one measurement arm 13. The two remaining outputs of the 3×3 monomode fibre coupler 9 are connected to in each case one detector 15 and 16 using in each case one radiation conductor 10b and 10b, which in turn is connected using signal technology to a detection electronic system 17. The detectors 15 and 16 measure the interference of the radiation reflected by the measurement object 19 with the reflected radiation in the reference arm 11 and/or 12.

The measurement arm 13 has a monomode fibre 14a, one end of which is connected to the monomode fibre coupler 9. The other end of the monomode fibre 14a is connected to a polarization controller 18, from which another monomode fibre 14b leads to a measurement head 20, which is described in detail below. The radiation then travels from the measurement head 20 as a free-space beam 22 to the measurement object 19 (here an eye).

The reference arms 11 and 12 have different optical base path lengths in accordance with the two measurement regions. The same path length variation element 23, which is rotatable about an element axis 21, acts in both reference arms 11 and 12.

The reference arms 11 and 12 are connected to the 3×3 monomode fibre coupler 9 via in each case one monomode fibre 25a and 26a. Connected to a polarization controller 27 and 29 is in each case that ends of the monomode fibre 25a and 26a which is remote from the monomode fibre coupler 9. In each case one monomode fibre 25b and 26b leads from the respective polarization controller 27 and 29 to an optical unit 31 and 32, which converts the radiation which is guided, among others, in the monomode fibre 25b or 26b into a free-space beam 33a and 35a. The two free-space beams 33a and 35a are guided, under a mutual offset angle W, onto the path length variation element 23 and are guided, from the path length variation element 23, provided it has a specific rotary position, described below, to in each case one mirror 37 and 39 in the optical unit 31 and 32 and is reflected back therefrom into the monomode fibre 25b and 26b; again via the path length variation element 23. The offset angle W is, within an angle tolerance, half as large as a corner angle δ of the path length variation element 23. The selected angle tolerance influences the available path length variation length. The larger the selected angle tolerance, the smaller the path length variation length. Since in the example chosen here a square cross section of the path length variation element 23 is chosen, the offset angle W is 45°. The path length variation element 23 chosen here has a refractive index of 1.5 and an edge width 1k of 14 mm, for example; for this reason, an angle tolerance of ±5° is used.

Each optical unit 31 and 32 has a ferrule 41a and 41b for gripping the end of the monomode fibre 25b and 26b that is remote from the polarization controller 27 and 29. Downstream of the ferrule 41a and 41b, the radiation guided in the monomode fibres 25b and 26b spreads out as a free-space beam 42a and 42b and is collimated using a lens unit 43a and 43b to form free-space beam 33a and 35a. The lens unit 43a and 43b can be an achromat, a single lens or a lens system. The beam that is reflected back by the respective mirror 37 and 39 is coupled from the lens unit 43a and 43b into the monomode fibre 25b and 26b via the ferrule 41a and 4b.

FIG. 2 shows an apparatus 50, presently suitable for the axial length measurements having a housing 57 and a metallic step 57.1 for receiving an adapter 60 with magnets 66 (see below), along an optical axis 58. Inside this step 57.1, a cutout 57.2, which is semicircular in axial cross-section, is formed for unique positioning of the adapter 60.

The apparatus 50 furthermore comprises an imaging optical unit 52 and an image recording unit 51, which are superposed with the beam path 58 of the interferometer 54 via a beam splitter 53. The light sources used here are LEDs 55 which are arranged concentrically around the beam path 58. In a biometer, this arrangement serves for the front imaging of the eye by photography. This can be utilized for example for documenting biometric examinations.

In the context of this embodiment of the invention, said components can also be used to detect the reflection of the structured illumination by the eye. As a result, the recording unit, consisting of the imaging optical unit 52 and the image recording unit 51, can assist both in the detection of the eye lengths (in the present case the first property) and in the detection of the topography (in the present case the second property), whereby the arrangement becomes particularly cost-effective.

Advantageous is an arrangement in which the axis for distance measurement is variable, such that a plurality of laterally offset and/or tilted distance measurements can be combined to one volume image. This can be achieved, for example, by inserting a pair of galvanically operated scanning mirrors into the beam path 59. A person skilled in the art will be able to see that such a movement of the measurement axis can also be achieved by way of a movement of the fixing aid for the eye or of a mechanical movement of the entire arrangement.

FIG. 3 shows a schematic front view of an apparatus 50 according to FIG. 2 in the direction of the optical axis 58. The figure illustrates that the step 57.1 is configured as a circularly ring-shaped step and comprises a semicircular cutout 57.2, with which the adapter 60, with annular flange 61 and a correspondingly shaped bulge 67 on the flange 61 (see FIG. 6), can be attached to the apparatus 50 in exactly one orientation. A person skilled in the art will also know further possibilities for achieving the unique orientation of the adapter 60 on the apparatus 50.

The apparatus 50 comprises LEDs 55, which are arranged in the shape of a ring. In the present FIG. 3, eight LEDs are shown, but a person skilled in the art will know that more or fewer LEDs can be provided. With preference, in particular between eight and 16 LEDs, with particular preference 12 LEDs, are arranged in the shape of a circle. It has proven expedient to distribute the light sources, for simplified data analysis, as one uniformly on one or more circle lines which are arranged concentrically with the axis of symmetry of the axial measurement.

The circle formed by the LEDs 55 has a smaller diameter than the step 57.1 and is orientated concentrically with respect to the step 57.1. The opening for the detector, or the image recording unit 51 and the interferometer 54, is located in the centre of the LED circle. Is also possible to use laser diodes which emit light in the visible or infrared spectral range instead of the LEDs, FIG. 4 shows a schematic illustration of a cross section of an adapter 6 for Placido ring projection, in the direction of the optical axis. The adapter 60 is configured as a mechanical add-on element for the apparatus 60 and uses the LEDs 55 of the apparatus 50 as a light source, that is to say in this embodiment, the adapter 60 does not comprise its own light source.

The adapter 60 has substantially the shape of a circular truncated cone, which comprises on the base area a short, straight cylindrical extension. During measurement, the narrow end of the adapter 60 or of the circular truncated cone faces the light to be measured. The adapter 60 comprises, on the cylindrical extension, a flange 61 or collar, which is formed as a counter piece to the step 57.1 of the apparatus 50. In addition, the flange 61 comprises a bulge 68 which is semicircular in radial cross section and during mounting comes to rest in the semicircular cutout 57.2 of the apparatus. Inside the cylindrical extension, a circularly ring-shaped Fresnel-lens-type profile 63 is arranged, which connects directly to a hollow cone-shaped optical waveguide 62. The optical waveguide 62 is preferably made of PMMA (polymethyl methacrylate), since PMMA can be processed particularly simply and is cheap. Other substances which transmit light at a given light frequency can of course also be used, for example glass or other plastics. The optical waveguide 62 is preferably enclosed in a metallic cladding. Instead of the metallic cladding, the hollow cone-shaped optical waveguide can also be coated merely on the outside, for example with a light-reflective coating such as for example a metal coating or a colour varnish.

The profile 62 serves for a more efficient coupling in of the light from the LEDs 55 of the apparatus into the optical waveguide 62. The profile 63, however, is not absolutely necessary for the function of the reflectometry module, and can therefore also be dispensed with, in particular if a sufficiently strong and homogeneous illumination device is present.

The optical waveguide 62 is configured as a hollow cone and has in turn a frustoconical hollow space which is coaxial with respect to the optical waveguide 62 or a conical cutout. That is to say, the hollow space or the cutout and the outer cladding of the optical waveguide 62 have a common axis of symmetry. The base area of the frustoconical hollow space is, however, located opposite the base area of the optical waveguide 62 and forms a distal end of the adapter 60, which is directed to the eyes during measurement. The hollow space then has alternating opaque regions 64 and light-transmissive regions 65. The light is now radiating out via these regions 64, 65 annularly in the axial direction of an eye to be measured (not illustrated).

Figure 5:
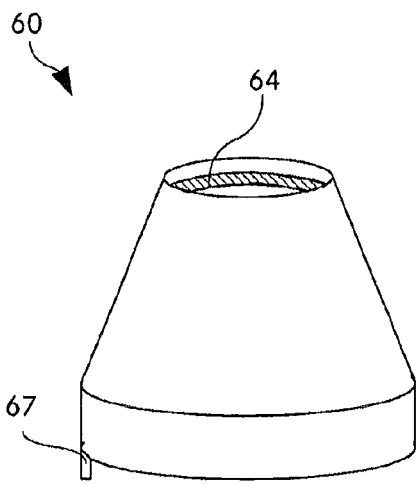
FIG. 5 a schematic oblique view of the adapter according to FIG. 4.

FIG. 5 illustrates a schematic oblique view of the adapter 60 according to FIG. 4. Illustrated here is the substantially circular frustoconical shape of the adapter 60.

Figure 6:
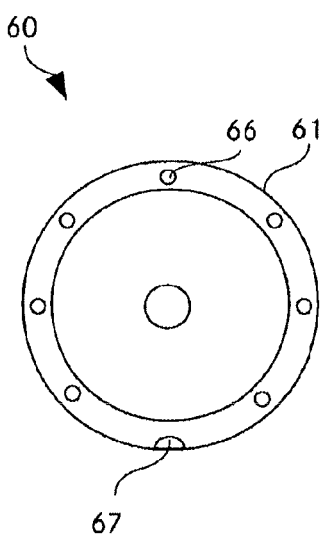
FIG. 6 a schematic rear view of an adapter according to FIG. 4 in the direction of the optical axis.

FIG. 6 shows a schematic rear view of an adapter according to FIG. 4 in the direction of the optical axis, that is to say the bottom view of the circular cylindrical extension. The figure shows the flange 61, which has in the edge region a semicircular bulge 67. The flange 61 comprises a plurality of, preferably seven, permanent magnets 66, via which the adapter 60 can be held on the metallic step 57.1 of the apparatus 50. In the centre, the opening can be seen, which in the mounted state communicates with the opening 56 of the apparatus and thus makes possible recording and analysis of the image data.

Figure 7:
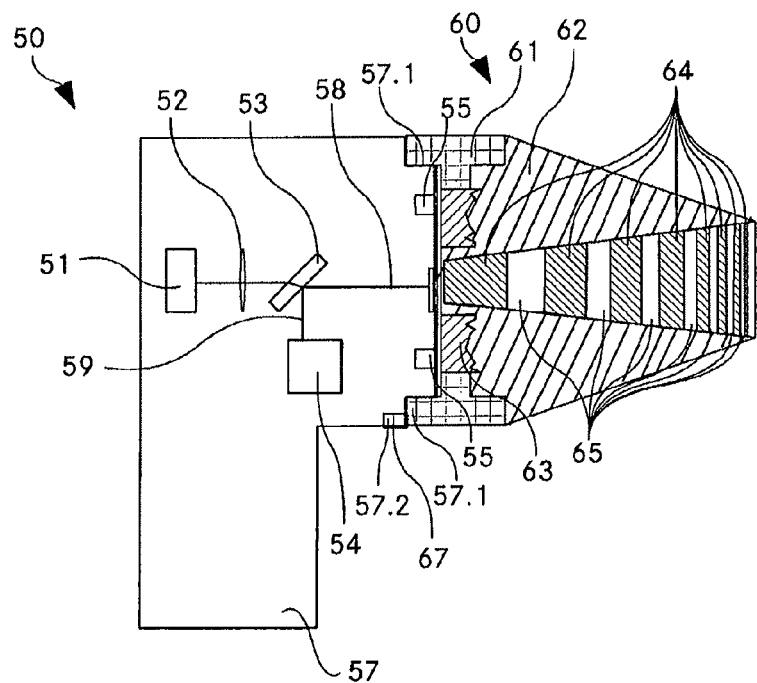
FIG. 7 a schematic illustration of a cross section through an arrangement comprising an apparatus for interferometric length measurements and an adapter, along an optical axis.

FIG. 7 shows a schematic illustration of a cross section through an arrangement comprising an apparatus 50 for interferometric length measurements and adapter 60, along an optical axis. The apparatus 50 here corresponds to FIG. 2, and the adapter 60 corresponds to FIG. 4. The flange 61 of the adapter 60 is here pushed onto the step 57.1 of the apparatus 50, such that the bulge 67 is located in the cutout 57.2 and fixes the adapter 60 with respect to rotation about its axis of symmetry. At the same time, the adapter 60 is held releasably on the metallic step 57.1 via the permanent magnets 66.

Figure 8:
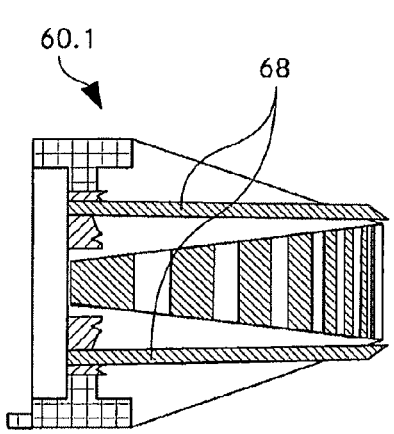
FIG. 8 a schematic illustration of a cross section of an adapter, substantially according to FIG. 4, comprising additional optical waveguides.
Figure 9:
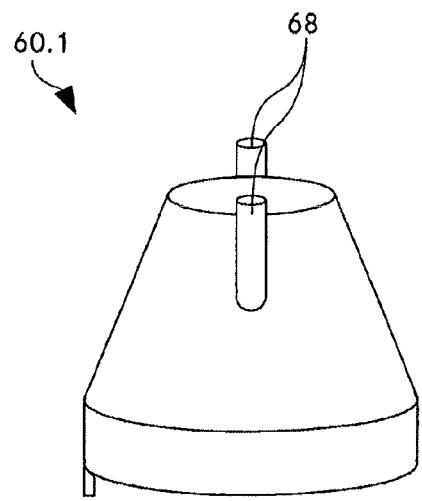
FIG. 9 a schematic oblique view of the adapter according to FIG. 8.

FIG. 8 shows a schematic illustration of a cross section of an adapter 60, substantially according to FIG. 4, but having two additional optical waveguides 68. Said optical waveguides are rod-shaped and substantially parallel to the axis of symmetry, but are arranged inside the adapter 60 such that they are slightly tilted in the distal direction towards the axis of symmetry. The optical waveguides 68 can be used to guide light from the LEDs 55 to the side of the adapter facing the eye. The eye-side radial distance from the measurement axis with normal measurement distance from the eye is preferably chosen to be such that direct reflection by the cornea front face does not reach the image recording unit, but the eye is illuminated indirectly by diffusely scattered light. FIG. 9 finally shows a schematic oblique view of the adapter according to FIG. 8.

The apparatus optionally has a signal transmitter (not illustrated), which signals to the control and analysis unit whether the adapter is connected to the apparatus. Said signal transmitter can be based for example on a mechanical switch, a light barrier or a magnetic switch. The control unit can use the signal to detect and carry out the respectively available measurement functions and to control the light sources and image recording unit specifically per context. The embodiment shown in FIG. 2 can, for example, when the adapter is attached (reflectometry module) carry out a cornea topography measurement, and when the adapter is removed a keratometry measurement, without expecting a corresponding pre-selection of the measurement function by the user. Illumination intensity and detection sensitivity can here be adjusted automatically to the value that is optimum for the respective measurement function.

In summary it should be noted that, according to the invention, an arrangement is provided which can be used to with low production costs simply either for measuring a length or a surface of an eye.

1 radiation source
3a-c monomode fibre
5 radiation attenuator
7 polarization controller
9 3×3 monomode fibre coupler
10a,b radiation conductor to 15 and 16
11 first reference arm
12 second reference arm
13 measurement arm
14a,b monomode fibre in 13
15 detector
16 detector
17 detection electronic system
18 polarization controller
19 measurement object
20 measurement head
21 element axis of 23
22 free-space beam between 20 and 19
23 path length variation element
25a,b monomode fibre in 11
26a,b monomode fibre in 12
27 polarization controller in 11
29 polarization controller in 12
31 optical unit in 11
32 optical unit in 12
33a-d free-space beam in 11
35a-d free-space beam in 12
37 mirror in 31
39 mirror in 32
41a,b ferrule
42a,b free-space beam between 43a/b and 41a/b
43a,b lens unit
45 rotation arrow
46 cross section of 23
50 apparatus for axial length measurements
51 image recording unit
52 imaging optical unit
53 beam splitter
54 interferometer
55 LED
56 opening
57 housing
57.1 step
57.2 semicircular cutout
58 beam path
59 beam path
60 adapter for reflectometry measurement
61 flange
62 optical waveguide
63 profile
64 opaque region of the conical cutout
65 light-transmissive region of the conical cutout
66 permanent magnet
67 semicircular bulge
68 optical waveguide

The invention claimed is:

1. Adapter for an apparatus for measuring a first property of an eye, wherein said adapter is releasably attached to the apparatus, and wherein, when the adapter is attached to the apparatus, a second, additional property of the eye is measurable.

2. Adapter according to claim 1, wherein at least one of the first and second properties is a geometric property of the eye.

3. Adapter according to claim 1, wherein the first property comprises a distance in an eye and the second property comprises at least a topography or a curvature of the eye.

4. Adapter according to claim 3, wherein the first property comprises at least one of the following lengths: cornea thickness, anterior chamber depth, lens thickness, eye length.

5. Adapter according to one of claims 1, wherein said adapter comprises a magnetic coupler attaching the adapter to the apparatus.

6. Adapter according to claim 1, wherein said adapter comprises a first optical waveguide for structured illumination of the eye.

7. Adapter according to claim 1, wherein said adapter comprises a second optical waveguide for diffuse or indirect illumination of the eye.

8. Apparatus for measuring properties of an eye, comprising an apparatus for measuring a first property of the eye, and an adapter according to claim 1 releasably attached to the apparatus, and wherein, when the adapter is attached to the apparatus, a second, property of the eye is measurable.

9. Apparatus according to claim 8, wherein the apparatus comprises an image recording unit with which, when the adapter is attached to the apparatus, a second property of the eye is measurable.

10. Apparatus according to claim 8, wherein the apparatus comprises a light source and the adapter comprises a first optical waveguide, wherein when the adapter is attached to the apparatus, light from the light source is guided to the eye via the first optical waveguide.

11. Apparatus according to claim 10, wherein the adapter comprises a second optical waveguide, with which light from a light source of the apparatus or of the adapter is guided to the eye for diffuse or indirect illumination.

12. Apparatus according to claim 8, wherein the adapter achieves structured illumination in the form of points or rings on the eye.

13. Apparatus according to claim 8, said apparatus further comprising a sensor for detecting the adapter.

14. Apparatus according to claim 13, said apparatus further comprising a control unit, wherein a measurement mode for the first property of the eye and a measurement mode for the second property of the eye are switchable by said control unit in response to said sensor.

15. Apparatus according to claim 8, wherein the apparatus comprises an interferometer.

16. Apparatus according to claim 15, wherein the interferometer is configured as a Fourier domain interferometer.

17. Apparatus according to claim 15, wherein the interferometer is pivotable or movable laterally with respect to the eye.

18. Apparatus according to claim 15, wherein the interferometer is configured as a Michelson interferometer.

19. Apparatus according to claim 8, comprising means for positioning at least one of the apparatus and the adapter with respect to the eye.

20. Apparatus according to claim 8, wherein the adapter is pivotably connected to the apparatus.

21. Method for measuring properties of an eye using an apparatus according to claim 8, wherein the adapter is releasably attached to the apparatus, and wherein the adapter is positioned in a beam path of the apparatus for measuring the second property of the eye.

22. Method according to claim 21, comprising the steps of:
   a. measuring a first property of the eye for obtaining first measurement values;
   b. positioning the adapter in dependence on the first measurement values.

23. Method according to claim 22, wherein the apparatus is used to determine a distance of the apparatus from the eye and the position of the adapter is monitored and set on the basis of said distance.

* * * * *